United States Patent [19]
Granz et al.

[11] Patent Number: 5,526,815
[45] Date of Patent: *Jun. 18, 1996

[54] THERAPY APPARATUS FOR LOCATING AND TREATING A ZONE LOCATED IN THE BODY OF A LIFE FORM WITH ACOUSTIC WAVES

[75] Inventors: Bernd Granz, Oberasbach; Ulrich Schaetzle, Roettenbach, both of Germany

[73] Assignee: Siemens Aktiengesellschat, Munich, Germany

[ * ] Notice: The term of this patent shall not extend beyond the expiration date of Pat. No. 5,435,304.

[21] Appl. No.: 164,723

[22] Filed: Dec. 10, 1993

[30] Foreign Application Priority Data

Jan. 29, 1993 [DE] Germany ............ 43 02 538.2

[51] Int. Cl.$^6$ .................................................. A61B 17/22
[52] U.S. Cl. ................... 128/660.03; 601/3; 601/4; 607/97; 128/661.01; 128/662.03
[58] Field of Search .................. 128/660.03, 660.07, 128/661.01, 662.03; 601/2–4; 607/97

[56] References Cited

U.S. PATENT DOCUMENTS

| | | |
|---|---|---|
| 4,159,462 | 6/1979 | Rocha et al. . |
| 4,526,168 | 7/1985 | Hassler et al. . |
| 5,036,855 | 8/1991 | Fry et al. . |
| 5,143,074 | 9/1992 | Dory . |
| 5,435,304 | 7/1995 | Oppelt et al. ............ 128/660.03 |

FOREIGN PATENT DOCUMENTS

| | | |
|---|---|---|
| 0194897 | 9/1986 | European Pat. Off. . |
| 0339693 | 11/1989 | European Pat. Off. . |
| 0444680 | 9/1991 | Germany . |
| 0S4213583 | 4/1993 | Germany . |

*Primary Examiner*—Ruth S. Smith
*Attorney, Agent, or Firm*—Hill, Steadman & Simpson

[57] ABSTRACT

A therapy apparatus for locating and treating a zone situated in the body of a subject life form with ultrasound includes an ultrasound transducer which can be optionally operated in a therapy mode or a locating mode, and which generates therapeutic ultrasound waves having a first frequency focused onto a zone of action in the therapy mode and generates diagnostic ultrasound having a second frequency in the locating mode. The ultrasound transducer also receives portions of the diagnostic ultrasound reflected in the body of the subject in the locating mode and converts them into electrical signals that are supplied to an evaluation electronics which provides image information about the zone to be treated.

17 Claims, 4 Drawing Sheets

THERAPY APPARATUS FOR LOCATING AND TREATING A ZONE LOCATED IN THE BODY OF A LIFE FORM WITH ACOUSTIC WAVES

BACKGROUND OF THE INVENTION

1. Field of the Invention

The present invention is directed to a therapy apparatus for locating and treating a zone in the body of a living subject with acoustic waves.

2. Description of the Prior Art

Devices of the type generally described above are known which include an electro-acoustic transducer that can be optionally operated in the therapy mode or the locating mode, which resonates in the therapy mode for producing therapeutic, acoustic waves focused onto a zone of action and resonates in the locating mode for producing diagnostic, acoustic waves. In the locating mode the transducer also receives parts of the diagnostic acoustic waves reflected in the body of the subject and converts them into electrical signals. Evaluation electronics, supplied with the received signals, provides image information about the zone to be treated.

Such therapy systems are employed, for example, for treating pathological tissue changes. The pathological tissue is thereby heated by focused ultrasound waves emitted as therapeutic acoustic waves. Insofar as the resulting tissue temperatures lie below 45° C., the cell metabolism is disturbed with the consequence that a retardation of the growth, or even an abatement, of the pathological tissue occurs in the case of tumors. This type of treatment is known as local hyperthermia. When temperatures beyond 45° C. are reached, the cell protein coagulates, with the consequence of necrotization of the tissue. This latter type of treatment is referred to as thermotherapy. The therapeutic acoustic waves are emitted as continuous sound that is always interrupted when the emission of diagnostic acoustic waves ensues.

A therapy system suitable for local hyperthermia or, for thermotherapy wherein separate transducers are provided for locating and therapy is disclosed in U.S. Pat. No. 5,036,855. This apparatus has an applicator head that accepts the transducers for locating and therapy and which can be introduced into body cavities.

Therapy devices of the type initially cited can also be employed in the treatment of stone maladies (lithotripsy) and bone conditions (osteorestoration). In these cases, the therapeutic acoustic waves are emitted, for example, in the form of shock waves.

Devices of the type initially cited are disclosed, for example, in U.S. Pat. No. 4,526,168 and by European Application 0 194 897. In both instances, it is not possible under all circumstances to identify the position of the zone to be respectively treated on the basis of the available image information with such precision that this zone can be positioned exactly in the effective region of the therapeutic acoustic waves.

SUMMARY OF THE INVENTION

It is an object of the present invention to provide an apparatus of the species initially cited with which a more exact locating and positioning of the zone to be treated is possible.

This object is achieved in a therapy apparatus for locating and treating a zone situated in the body of a living subject with acoustic waves having the following features. An electro-acoustic transducer is provided which can be optionally operated in a therapy mode or a locating mode. The transducer generates therapeutic acoustic waves focused onto a zone of action in the therapy mode having a first frequency and generates diagnostic acoustic waves in the locating mode having a second frequency, and receives portions of the diagnostic acoustic waves reflected in the body of the subject in the locating mode and converts them into electrical signals. Evaluation electronics provides image information about the zone to be treated on the basis of the electrical signals supplied to it. The zone of action or the center thereof and the zone to be treated can then be made to coincide.

In the therapy apparatus of the invention, thus, it is possible to match the frequency of the generated acoustic waves optimally to the requirements of the therapy mode as well as to the requirements of the locating mode. This represents a substantial advantage over known systems because, first, the topical resolution achieved in the locating mode, and thus the precision obtainable in the locating and positioning, and second, the attenuation that the acoustic waves experience in the subject to be treated, are dependent on the frequency of the acoustic waves. It is advantageous for the therapy mode, to achieve a time-saving treatment and an optimally low dose of acoustic energy supplied to the patient when the attenuation of the acoustic waves in the subject to be treated is as low as possible. During the locating mode, a higher attenuation of the acoustic waves does not intrinsically represent a problem, as long as it is assured that the reflected parts thereof reach the electro-acoustic transducer with adequate amplitude. However, the spatial resolution should be as high as possible. In a preferred embodiment of the invention the frequency of the diagnostic acoustic waves is higher than the frequency of the therapeutic acoustic waves, as disclosed in European Application 03 39 693 in conjunction with a therapy apparatus having separate transducers for locating and therapy. The therapy mode is then especially effective as a consequence of a low attenuation of the acoustic waves in the subject to be treated. A high spatial resolution, and thus a high precision of the locating and positioning procedure, is achieved in the locating mode.

An ultrasound transducer, particularly a piezoelectric ultrasound transducer, is provided as the electro-acoustic transducer, oscillating in the thickness mode and having a basic resonant mode in which it oscillates at a frequency that, in the material of the ultrasound transducer, corresponds to a wavelength that is equal to twice the thickness of the ultrasound transducer. The aforementioned first and second frequencies in the material of the ultrasound transducer correspond to wavelengths that are the product of an uneven number and the wavelength of the fundamental mode. This embodiment makes use of the fact that ultrasound transducers oscillating in the thickness mode also oscillate at their $3/2\lambda$ harmonic, $5/2\lambda$ harmonic, etc. in addition to oscillating at their fundamental frequency, referred to as the $\lambda/2$ mode. Good efficiency in the emission of the acoustic waves is thus achieved for the first as well as for the second frequency since, first, the parts of the acoustic waves emitted toward the back of the transducer can also be utilized and, second the ultrasound transducer oscillates at its natural mode as a consequence of the first and second frequencies selected as described.

The image information, moreover, can be provided in the form of A, B or C mode ultrasound images, preferably in real time.

In a further version of the invention the ultrasound transducer is fashioned as a phased array comprising a plurality of ultrasound transducer elements. In this case, it is easily possible in a known way, first, to displace the zone of action of the therapeutic acoustic waves electronically so as to correspond to requirements during the therapy mode, and second, to scan the subject to be treated with the diagnostic acoustic waves during the locating mode in the manner required for producing a B or C mode ultrasound image.

When the ultrasound transducer is fashioned as a phased array, in a preferred embodiment of the invention a plurality of ultrasound transducer elements immediately neighboring one another are connected in parallel in the therapy mode to form an ultrasound transducer element group, and the ultrasound transducer elements of an ultrasound transducer element group oscillate without a phase difference. It is then possible to allocate a shared delay element to an ultrasound transducer element group during the therapy mode. Therefore respective arrangements of delay elements can be provided for the locating mode and for the therapy mode. This measure, however, can also be meaningful in view of the different amplitudes of the electrical signals that drive the ultrasound transducer elements during the therapy and locating modes. Generally, it will suffice to implement the ultrasound transducer as a linear arrangement of a plurality of ultrasound transducer elements (referred to as a linear array), since it is then possible in the locating mode to deflect the diagnostic acoustic waves in the respective way required for producing a sector scan, or to implement a linear scan. Fundamentally, however, matrix-like arrangements of the ultrasound transducer elements can alternatively be employed, which enable a three-dimensional scanning or displacement of the zone of action.

DESCRIPTION OF THE PREFERRED EMBODIMENTS

Figure 1:
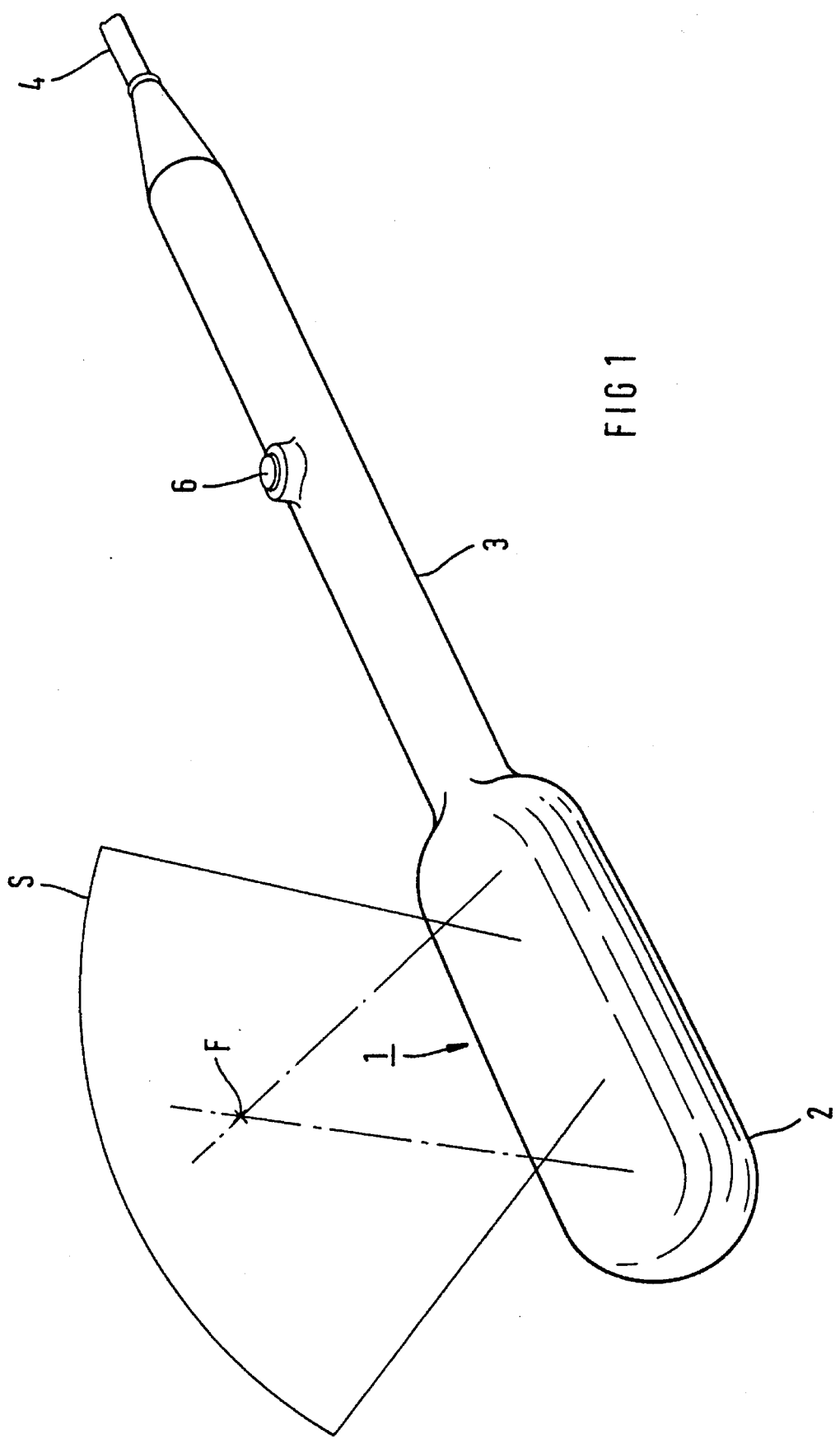
FIG. 1 is a perspective illustration of a handpiece of a therapy apparatus constructed in accordance with the principles of the present invention containing the electro-acoustic transducer.

The invention shall be set forth in greater detail below with reference to the example of a therapy apparatus of the invention shown in the drawings, provided for treatment of benign prostate hyperplasia.

FIG. 1 shows a handpiece 1 of a therapy apparatus of the invention for treatment of benign prostate hyperplasia, the handpiece 1 being adapted for rectal application. The handpiece 1 is approximately spoon-shaped and has an approximately oval, flat application end 2 to which a handle 3 is attached. The application end, which has a thickness of approximately 15 mm, a width of approximately 30 mm and a length of approximately 60 mm, is provided for introduction into the rectum of the patient to be treated, the handle 3 of the handpiece 1 then projecting therefrom. The handpiece 1 is connected via a connecting cable 4 to the remaining elements of the therapy apparatus shown in FIG. 3.

The handpiece 1 contains an ultrasound transducer 5 (shown in greater detail in FIG. 2) in its application end, which is filled with an acoustic propagation medium, for example water. A switch 6 with which the attending physician can switch the therapy apparatus from the locating mode to the therapy mode is attached in the region of the handle 3 of the handpiece 1. The therapy mode is switched on by pressing the switch 6, whereas the locating mode is switched on when the switch 6 is not actuated.

In the locating mode, the ultrasound transducer 5 generates diagnostic acoustic waves in the form of short ultrasound pulses whose length amounts to a few half cycles. In the therapy mode, the ultrasound transducer 5 additionally produces focused, therapeutic acoustic waves in the form of ultrasound waves. The ultrasound waves are continuous sound or of pulsed, i.e., continuous sound that is briefly interrupted by short pulse press for the emission of the diagnostic ultrasound waves, which are likewise focused.

Figure 2:
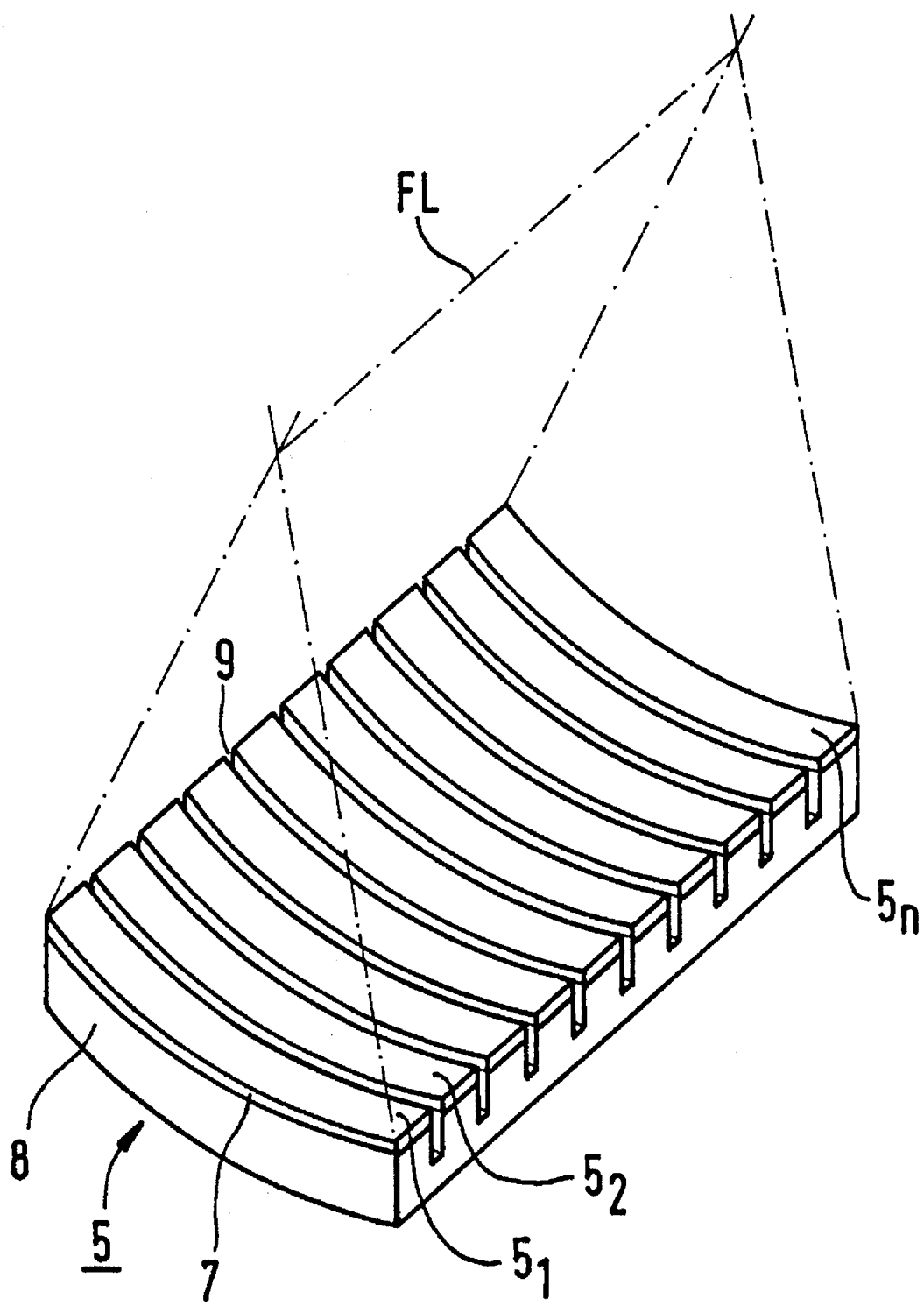
FIG. 2 is a perspective illustration of the electro-acoustic transducer contained in the handpiece shown in FIG. 1.

According to FIG. 2, the ultrasound transducer 5 is constructed as a linear array, i.e. the ultrasound transducer 5 is subdivided into a plurality of ultrasound transducer elements $5_1$, $5_2$, etc., through $5_n$. The subdivision is implemented such that it is possible to individually drive each of the ultrasound transducer elements $5_1$ through $5_n$ to produce ultrasound waves by supplying a suitable electrical signal. In the way required in locating mode, it is likewise possible to separately tap the electrical signals for the individual ultrasound transducer elements $5_1$ through $5_n$ that arise due to the reception of the parts of the diagnostic ultrasound waves reflected in the body of the subject to be treated.

For clarity, the ultrasound transducer in FIG. 2 is shown as being subdivided only into a few (ten) ultrasound transducer elements. In practice, the ultrasound transducer 5 is subdivided, for example, into 128 or 256 ultrasound transducer elements. The ultrasound transducer 5 is constructed in a known way such that the actual piezoelectric material 7, in the form a layer of a constant thickness, is applied on a carrier member 8 that likewise has a constant thickness and is well-matched in terms of mechanical impedance. The connection of the layer 7 of piezoelectric material to the carrier member 8 ensues on the basis of a metallic layer (not shown) whose thickness is small in comparison to that of the layer 7. The surface of the layer 7 facing away from the carrier member 8 is likewise provided with a thin metallic layer (not shown). The metallic layers serve as electrodes for the electronic contacting of the ultrasound transducer elements $5_1$ through $5_n$.

In order to obtain ultrasound transducer elements $5_1$ through $5_n$ that can be driven independently of one another and whose output signals can be tapped (sampled) independently of one another, the piezoelectric layer 7 connected to the carrier member 8 is subdivided into the individual ultrasound transducer elements $5_1$ through $5_n$ by narrow incisions that proceed transversely relative to the longitudinal axis of the ultrasound transducer 5; one of these is referenced 9 in FIG. 2. In order to mechanically decouple the ultrasound transducer elements $5_1$ through $5_n$ from one another, the incisions 9 have a depth that is clearly greater than the thickness of the piezoelectric layer 7.

Given a suitable drive of the individual ultrasound transducer elements $5_1$ through $5_n$, it is possible to focus the ultrasound waves emitted by the ultrasound transducer 5, or to cause them to execute a scan motion, for example in the sense of a sector scan. As is known, focusing or the execution of a scan motion is only possible in these circumstances in the direction of the longitudinal axis of the ultrasound transducer 5, or of the linear array. In order also to achieve a focusing transversely relative thereto, the ultrasound transducer 5 is cylindrically curved around an axis that proceeds parallel to its longitudinal axis in the manner disclosed by U.S. Pat. No. 4,149,462 in conjunction with diagnostic ultrasound transducers, so that, given simultaneous drive of all ultrasound transducer elements $5_1$ through $5_n$, focusing of the ultrasound waves on a line-shaped zone of action referenced FL in FIG. 2 is achieved. The line-shaped zone of action FL proceeds parallel to the longitudinal axis of the ultrasound transducer 5 or of the linear array. Given drive of the ultrasound transducer 5 in the fashion of a phased array, a body slice which is, for example, sector shaped, of the subject to be treated can be scanned for locating purposes. A corresponding sector is indicated in FIG. 1 and is referenced S. During the therapy mode, the center of the selected treatment zone, referenced F in FIG. 1, can be displaced in the middle plane of the sector-shaped slice.

Details of the drive of the ultrasound transducer elements $5_1$ through $5_n$ shall be set forth in greater detail below with reference to FIG. 3. The ultrasound transducer elements $5_1$ through $5_6$ and $5_{n-2}$ through $5_n$ of the ultrasound transducer elements $5_1$ through $5_n$ are shown therein as an example. These are respectively connected via lines $4_1$ through $4_n$ of the connecting cable 4 to switches $10_1$ through $10_n$. The switches $10_1$ through $10_n$ are components of control and image-generating electronics, generally referenced 11. The switches $10_1$ through $10_n$, which are preferably electronic switches, are actuated such by a drive unit 12 such that all switches $10_1$ through $10_n$ each assume the same switch position. This is illustrated in FIG. 3 by showing the switches $10_1$ through $10_n$ connected to one another by a broken line.

Figure 3:
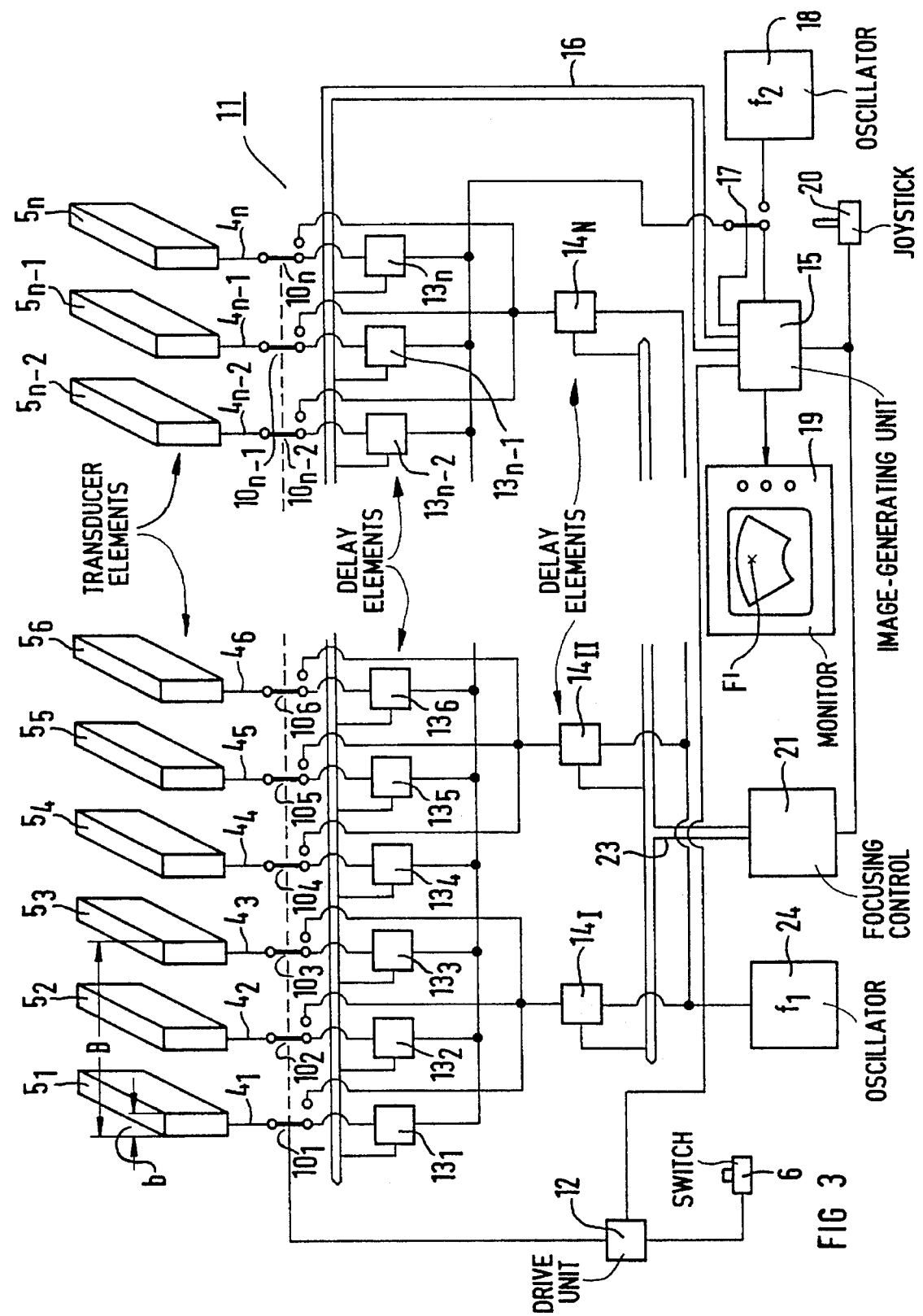
FIG. 3 shows a block diagram of the therapy apparatus.

When the switches $10_1$ through $10_n$ assume their switch position shown in FIG. 3, corresponding to the locating mode, each of the ultrasound transducer elements $5_1$ through $5_n$ is connected to a corresponding delay element $13_1$ through $13_n$. When, by contrast, the switches $10_1$ through $10_n$ assume their other switch position, which corresponds to the therapy mode, three ultrasound transducer elements, for example the ultrasound transducer elements $5_4$ through $5_6$ are connected as a group to a different delay element, for example to the delay element $14_{II}$. Thus the ultrasound transducer elements $5_1$ through $5_n$ are combined in the therapy mode to form groups consisting of three ultrasound transducer elements each, these being referenced I through N in FIG. 3. The transducer elements forming each group are neighboring elements, i.e., they constitute a consecutive sub-sequence within the overall sequence $5_1$ to $5_n$. The corresponding delay elements are referenced $14_1$ through $14_N$.

The delay times of the delay elements $13_1$ through $13_n$ are individually set by an image-generating circuit 15 via a line bus 16. The setting of the delay times ensues such that a sector-shaped body slice of the subject to be treated is scanned according to FIG. 1 when the delay elements $13_1$ through $13_n$ are connected in alternation to an oscillator 18 or to the image-generating circuit 15 with the switch 17 actuated by the image-generating circuit 15. The corresponding ultrasound image is displayed on a monitor 19 connected to the image-generating circuit 15.

When the ultrasound transducer elements $5_1$ through $5_n$ are connected via the delay elements $13_1$ through $13_n$ and the switch 17 to the oscillator 18, then they are driven by the oscillator 18 to generate an ultrasound pulse. Immediately following the image-generating circuit 15 changes the switch position of the switch 17, so that the electrical signals corresponding to the reflected parts of the ultrasound pulse received with the ultrasound transducer elements $15_1$ through $15_n$ arrive at the image-generating circuit 15 via the delay elements $13_1$ through $13_n$ and via the switch 17. The delay times of the delay elements $13_1$ through $13_n$ are thereby set such that the emission of the ultrasound pulse ensues in a first direction. This procedure is multiply repeated, for example 256 times, however, the image-generating circuit 15 modifies the delay times upon every repetition of this procedure such that the emission direction of the ultrasound pulse is modified until the entire sector-shaped body slice is scanned. In a known way, the image-generating circuit produces a B-mode ultrasound image from the electrical signals obtained in this manner. During the locating mode, the described sequence is repeated anew, so that an up-dated ultrasound image is produced.

A joystick 20, with which it is possible to displace a mark F' mixed into the ultrasound image displayed on the monitor 19, is connected to the image-generating circuit 15. A focusing control 21, which is likewise connected to the joystick 20, then sets the individual delay times of the delay elements $14_1$ through $14_N$ via a line bus 23 so that the therapeutic ultrasound waves emanating from the ultrasound transducer elements $5_1$ through $5_n$, driven with an oscillator 24, are focused onto a zone of action when the switches $10_1$ through $10_n$ are brought into their position corresponding to the therapy mode. The center F of the zone of action lies in the body of the subject to be treated at that location which corresponds to the location marked in the ultrasound image with the mark F'.

The therapeutic ultrasound waves are a matter of continuous sound or of pulsed continuous sound. In the therapy mode, which, as already mentioned, is switched on by actuating the switch 6, the therapeutic ultrasound waves are periodically briefly interrupted in order also to update the ultrasound image during the therapy mode. To this end, the image-generating circuit 15 acts on the drive unit 12 and brings the switches $10_1$ through $10_n$ into the position corresponding to the locating mode for a time required for the generating of an ultrasound image. Thereafter, the switches return into the switch position corresponding to the therapy mode until the preparation of the following ultrasound image. Whereas the ultrasound images in the locating mode are generated with a repetition rate of, for example, 25 Hz, the repetition rate in the therapy mode lies, for example, at 0.2 through 1 Hz.

In the therapy mode, the oscillator 24 drives the ultrasound transducer elements to generate therapeutic ultrasound waves having a first frequency f1 which is lower than the frequency f2 of the diagnostic ultrasound waves that the ultrasound transducer elements $5_1$ through $5_n$ generate in the locating mode when driven by the oscillator 18. When producing the ultrasound images, it is thus possible to achieve a high topical resolution, so that it is possible to locate the zone to be treated with enhanced precision and to position the zone of action in the zone to be treated with enhanced precision. At the same time, it is assured that the therapeutic ultrasound waves are not unnecessarily attenuated.

The width b of the ultrasound transducer elements $5_1$ through $5_n$ is selected to be smaller than half the wavelength of the diagnostic ultrasound waves in the acoustic propagation medium, i.e. in the propagation medium contained in the handpiece 1, or in the body tissue of the subject to be treated. It is thereby assured that the emission of the diagnostic ultrasound waves ensues with a non-directional beam pattern, this being a prerequisite for being able to scan a sector-shaped body slice of a subject to be treated in the way set forth.

The number of ultrasound transducer elements that are connected in parallel to form an ultrasound transducer element group is selected such that the width B of the ultrasound transducer element group is smaller than half the wavelength of the therapeutic ultrasound waves in the respective acoustic propagation medium. The emission of the therapeutic ultrasound waves then ensues non-directionally, this being a prerequisite for being able to displace the zone of action in the described way.

The ultrasound transducer 5, or the transducer elements $5_1$ through $5_n$ thereof, are ultrasound resonators that execute thickness oscillations. As is known, such an ultrasound transducer has, or such ultrasound transducer elements have a fundamental resonance at a frequency having a wavelength that is equal to twice the thickness of the ultrasound transducer. Further resonances occur at harmonics having wavelengths respectively corresponding to the product of an uneven number and the wavelength of the fundamental resonance. In order to assure that the emission of the therapeutic waves as well as of the diagnostic waves ensues with a high efficiency, the first frequency $f_1$ and the second frequency $f_2$ in the therapy apparatus of the invention are selected such that the respectively corresponding wavelengths in the material of the ultrasound transducer elements $5_1$ through $5_n$, are the product of a first uneven number and the wavelength of the fundamental resonance and the product of a second uneven number and the wavelength of the fundamental resonance. The ultrasound transducer elements $5_1$ through $5_n$ then operate under resonant conditions both in the therapy mode and in the locating mode.

For implementing a treatment, the application end 2 of the handpiece 1 is introduced into the rectum of the patient. The switch 6 is initially not actuated. The apparatus is thus in the locating mode. The handpiece 1 is then aligned such that the subject to be treated appears in the ultrasound image. The attending physician now sets the mark F' onto the zone to be treated, using the joystick 20. He or she then presses the switch 6 at the handle 3, causing a switch to the therapy mode. Therapeutic ultrasound waves are then emitted, their zone of action being at a position in the subject to be treated that its center F coincides with the location corresponding to the established position of the mark F'. Since brief-duration switches into the locating mode are constantly undertaken during the therapy in the above-described way, the viewer receives the impression of a real-time display and is constantly informed of the therapeutic success. Since the ultrasound transducer 5 is situated in the handpiece 1, it is easily possible to displace the zone of action during the therapy, so that the position of the zone of action can be recognized at any time on the basis of the mark mixed into the ultrasound image.

The therapy mode is ceased when the switch 6 is again released. The apparatus then continues to run in the locating mode on its own.

Figure 4:
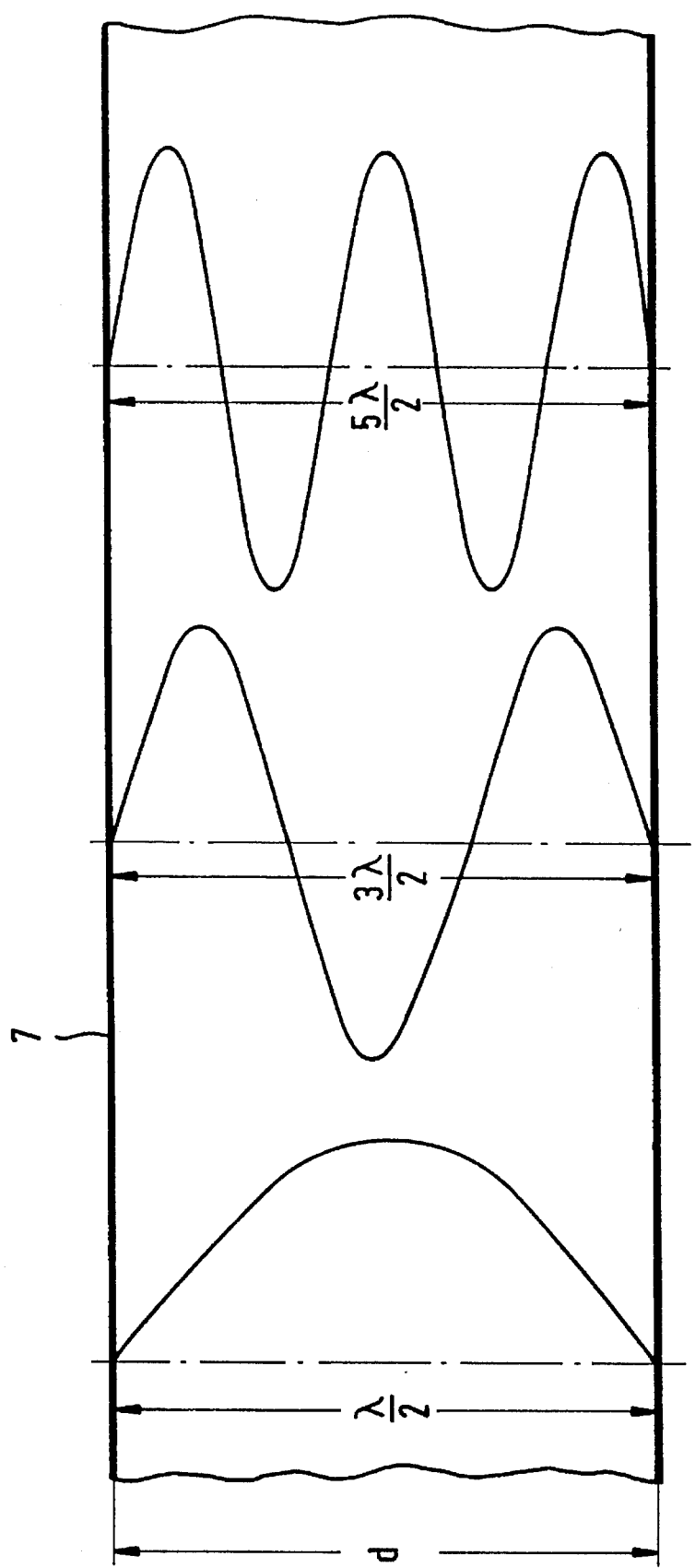
FIG. 4 illustrates two different operating conditions of the therapy apparatus of the invention.

An ultrasound transducer 5 whose fundamental resonance lies at 1.5 MHz is suitable for treatment of benign prostate hyperplasia. The ultrasound transducer 5 is likewise operated in the therapy mode at this frequency as the first frequency f1. In the locating mode, the ultrasound transducer 5 is operated at its 3/2λ resonance, i.e. the second frequency f2 lies at 4.5 MHz. The corresponding conditions are shown in FIG. 4.

When a sound propagation speed of 1,500 m/sec is assumed for the tissue of the subject to be treated and for the acoustic propagation medium situated in the handpiece 1, then the width b of the ultrasound transducer elements $5_1$ through $5_n$ of the ultrasound transducer 5 should not exceed 0.17 mm in order to assure that no directional emission of the diagnostic acoustic waves ensues. It is simultaneously assured given this width b of the individual ultrasound transducer elements $5_1$ through $5_n$ that the emission of the therapeutic ultrasound waves also ensues non-directionally, since the width B of the ultrasound transducer element groups I through N, each comprising three ultrasound transducer elements, does not exceed 0.5 mm.

The sound propagation speed lies at approximately 4,000 m/sec in standard piezoceramic materials. Consequently, the ultrasound transducer elements $5_1$ through $5_n$ must have a thickness d on the order of magnitude of 1.3 mm in order to operate at the aforementioned values of the first and second frequencies.

The above-described exemplary embodiment is directed to a therapy apparatus that is rectally applied, i.e. is employed partially invasively and is provided for the treatment of benign prostate hyperplasia. However, other therapy systems that are applied extracorporeally, i.e. non-invasively, and/or serve the purpose of treating other maladies can also be fashioned in accordance with the principles of the present invention.

As used herein, a phased array means an arrangement of a plurality of ultrasound transducer elements that can be electronically focused by chronologically delayed drive signals. A linear array means a linear arrangement of a plurality of ultrasound transducer elements. A scan means, for example, conducting linear or sector-shaped scanning with an ultrasound beam.

Although modifications and changes may be suggested by those skilled in the art, it is the intention of the inventors to embody within the patent warranted hereon all changes and modifications as reasonably and properly come within the scope of their contribution to the art.

We claim as our Invention:

1. A therapy apparatus for locating and treating a zone situated in the body of a subject with acoustic waves, said apparatus comprising:

electro-acoustic transducer means for converting incoming electrical signals into outgoing acoustic waves and for converting incoming acoustic waves into outgoing electrical signals;

means for operating said transducer means in a therapy mode for generating acoustic waves at a first frequency focused onto a zone of action;

means for operating said transducer means in a locating mode for generating diagnostic acoustic waves at a second frequency which is higher than said first frequency and for receiving incoming diagnostic acoustic waves reflected in the body of said subject, said transducer means generating outgoing diagnostic electrical signals corresponding to said incoming diagnostic acoustic waves; and evaluation means for generating an image from said diagnostic electrical signals, said image including a zone of said subject to be treated with said therapeutic acoustic waves.

2. A therapy apparatus as claimed in claim 1 wherein said transducer means comprises an ultrasound transducer having a thickness and which exhibits thickness oscillations when operated by said means for operating said transducer means in said therapy mode and said means for operating said transducer means in said locating mode, said ultrasound transducer having a fundamental resonance at which said ultrasound transducer oscillates at a frequency having a wavelength which is equal to twice the thickness of said ultrasound transducer, and wherein said first frequency has a wavelength which is the product of the wavelength of said fundamental resonance and a first uneven number, and wherein said second frequency has a wavelength which is the product of the wavelength of said fundamental resonance and a second uneven number.

3. A therapy apparatus as claimed in claim 1 wherein said transducer means comprises a phased array consisting of a plurality of ultrasound transducer elements.

4. A therapy apparatus as claimed in claim 3 wherein said plurality of ultrasound transducer elements comprise a sequence including a plurality of subsequences, and further comprising means for oscillating all transducer elements in a subsequence without phase difference during said therapy mode.

5. A therapy apparatus as claimed in claim 4 wherein said means for oscillating includes a common delay element connected to each ultrasound transducer element in a subsequence during said therapy mode.

6. A therapy apparatus as claimed in claim 5 wherein said means for operating said transducer means in said locating mode includes a first set of delay elements respectively connected to said ultrasound transducer elements, and wherein said means for operating said transducer means in said therapy mode includes a second set of delay elements respectively connected to all ultrasound transducer elements in each subsequence.

7. A therapy apparatus as claimed in claim 3 wherein said phased array comprises a linear array.

8. A therapy apparatus as claimed in claim 7 wherein said linear array has a longitudinal axis, and has a concave curve around a curvature axis extending parallel to said longitudinal axis.

9. A therapy apparatus as claimed in claim 7 wherein said means for operating said transducer means in said locating mode comprises means for conducting a linear scan using said linear array.

10. A method for locating and treating a zone situated in the body of a subject with acoustic waves, said method comprising the steps of:
  using an electro-acoustic transducer for converting incoming electrical signals into outgoing acoustic waves and for converting incoming acoustic waves into outgoing electrical signals;
  operating said transducer in a therapy mode for generating acoustic waves at a first frequency focused onto a zone of action;
  operating said transducer in a locating mode for generating diagnostic acoustic waves at a second frequency which is higher than said first frequency and for receiving incoming diagnostic acoustic waves reflected in the body of said subject, said transducer generating outgoing diagnostic electrical signals corresponding to said incoming diagnostic acoustic waves; and
  generating an image from said diagnostic electrical signals, said image including a zone of said subject to be treated with said therapeutic acoustic waves.

11. A method as claimed in claim 10 wherein said transducer has a thickness and exhibits thickness oscillations when operated in said therapy mode and in said locating mode, said transducer having a fundamental resonance at which said transducer oscillates at a frequency having a wavelength which is equal to twice the thickness of said transducer, and wherein the step of operating said transducer in said therapy mode at a first frequency is further defined by operating said transducer at a first frequency having a wavelength which is the product of the wavelength of said fundamental resonance and a first uneven number, and wherein the step of operating said transducer in said locating mode at a second frequency is further defined by operating said transducer at a second frequency having a wavelength which is the product of the wavelength of said fundamental resonance and a second uneven number.

12. A method as claimed in claim 10 wherein said transducer comprises a sequence of transducer elements including a plurality of sub-sequences of transducer elements, and wherein the step of operating said transducer in said locating mode is further defined by oscillating all transducer elements with a phase difference and wherein the step of operating said transducer in said therapy mode is further defined by oscillating all transducer elements in a sub-sequence without phase difference during said therapy mode.

13. A method apparatus as claimed in claim 12 wherein the step of oscillating all transducer elements in a sub-sequence without phase difference is further defined by connecting a common delay element to each transducer element in a sub-sequence during said therapy mode.

14. A method as claimed in claim 12 wherein the step of oscillating said transducer elements in said locating mode is further defined by respectively connecting a first set of delay elements to said transducer elements, and wherein the step of oscillating said transducer elements in said therapy mode is further defined by respectively connecting a second set of delay elements to all transducer elements in each subsequence.

15. A method as claimed in claim 10 wherein said transducer comprises a linear array of transducer elements and wherein the step of operating said transducer in said locating mode is further defined by conducting a linear scan using said linear array.

16. A therapy apparatus for locating and treating a zone situated in the body of a subject with acoustic waves, said apparatus comprising:
  a phased array consisting of a plurality of ultrasound transducer elements forming electro-acoustic transducer means for converting incoming electrical signals into outgoing acoustic waves and for converting incoming acoustic waves into outgoing electrical signals said transducer elements comprising a sequence including a plurality of sub-sequences;
  means for operating said transducer means in a therapy mode for generating acoustic waves at a first frequency focused onto a zone of action including means for oscillating all transducer elements in a sub-sequence without phase difference during said therapy mode;
  means for operating said transducer means in a locating mode for generating diagnostic acoustic waves at a second frequency and for receiving incoming diagnostic acoustic waves reflected in the body of said subject, said transducer means generating outgoing diagnostic electrical signals corresponding to said incoming diagnostic acoustic waves, said means for operating said transducer means in said locating mode including a first set of delay elements respectively connected to said ultrasound transducer elements;
  said means for operating said transducer elements in said therapy mode including a second set of delay elements respectively connected to all ultrasound transducer elements in each sub-sequence; and
  evaluation means for generating an image including a zone of said subject to be treated with said therapeutic acoustic waves from said diagnostic electrical signals.

17. A method for locating and treating a zone situated in the body of a subject with acoustic waves, said method comprising the steps of:

providing an electro-acoustic transducer formed by a phased array including a plurality of transducer elements comprising a sequence including a plurality of sub-sequences;

using said electro-acoustic transducer for converting incoming electrical signals into outgoing acoustic waves and for converting incoming acoustic waves into outgoing electrical signals;

providing a first set of delay elements including a plurality of delay elements respectively connectable to said transducer elements and providing a second set of delay elements respectively connectable to all transducer elements in each sub-sequence;

operating said transducer in a therapy mode by oscillating all transducers in each sub-sequence without delay by connecting said transducer elements to said second set of delay elements for generating acoustic waves at a first frequency focused onto a zone of action;

operating said transducer in a locating mode by oscillating all of said transducers with a delay by connecting said transducers to said first set of delay elements for generating diagnostic acoustic waves at a second frequency and for receiving incoming diagnostic acoustic waves reflected in the body of said subject, said transducer generating outgoing diagnostic electrical signals corresponding to said incoming diagnostic acoustic waves; and generating an image from said diagnostic electrical signals, said image including a zone of said subject to be treated with said therapeutic acoustic waves.

* * * * *